(12) United States Patent
Liphardt

(10) Patent No.: US 8,345,241 B1
(45) Date of Patent: *Jan. 1, 2013

(54) APPLICATION OF DIGITAL LIGHT PROCESSOR IN IMAGING ELLIPSOMETER AND THE LIKE SYSTEMS

(75) Inventor: Martin M. Liphardt, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 337 days.

This patent is subject to a terminal disclaimer.

(21) Appl. No.: 12/806,380

(22) Filed: Aug. 11, 2010

Related U.S. Application Data

(63) Continuation-in-part of application No. 12/002,650, filed on Dec. 18, 2007, now Pat. No. 7,777,878.

(60) Provisional application No. 60/875,599, filed on Dec. 19, 2006.

(51) Int. Cl.
*G01J 4/00* (2006.01)

(52) U.S. Cl. ........................................ 356/369

(58) Field of Classification Search ........................ None
See application file for complete search history.

(56) References Cited

U.S. PATENT DOCUMENTS

| | | | |
|---|---|---|---|
| 4,114,366 A | 9/1978 | Renner et al. | 368/68 |
| 5,517,312 A | 5/1996 | Finarov | 356/630 |
| 5,909,559 A | 6/1999 | So | 710/307 |
| 5,932,119 A | 8/1999 | Kaplan et al. | 219/121.68 |
| 5,963,326 A | 10/1999 | Masao | 356/369 |
| 6,028,671 A | 2/2000 | Svetkoff et al. | 356/368 |
| 6,061,049 A | 5/2000 | Pettitt et al. | 345/691 |
| 6,105,119 A | 8/2000 | Kerr et al. | 711/219 |
| 6,163,363 A | 12/2000 | Nelson et al. | 355/32 |
| 6,179,489 B1 | 1/2001 | So et al. | 718/102 |
| 6,200,646 B1 | 3/2001 | Neckers et al. | 427/510 |
| 6,259,153 B1 | 7/2001 | Corisis | 257/666 |
| 6,275,271 B1 | 8/2001 | Hitomi et al. | 348/743 |
| 6,298,370 B1 | 10/2001 | Tang et al. | 718/102 |
| 6,398,389 B1 | 6/2002 | Bohler et al. | 362/293 |
| 6,459,425 B1 | 10/2002 | Holub et al. | 345/207 |
| 6,496,447 B1 | 12/2002 | Gabriel | 370/228 |
| 6,558,006 B2 | 5/2003 | Ioka | 353/94 |
| 6,583,921 B2 | 6/2003 | Nelson | 359/291 |
| 6,618,186 B2 | 9/2003 | Kaeriyama | 359/292 |
| 6,619,804 B2 | 9/2003 | Davis et al. | 353/98 |
| 6,654,516 B2 | 11/2003 | So | 385/27 |
| 6,658,063 B1 | 12/2003 | Mizoguchi et al. | 375/260 |
| 6,663,560 B2 * | 12/2003 | MacAulay et al. | 600/160 |
| 6,665,110 B2 | 12/2003 | Pettitt | 359/291 |
| 6,741,503 B1 | 5/2004 | Farris et al. | 365/189.05 |
| 6,758,571 B2 | 7/2004 | Heaton | 359/872 |
| 6,781,094 B2 | 8/2004 | Harper | 219/121.72 |
| 6,842,549 B2 | 1/2005 | So | 385/15 |
| 6,853,454 B1 * | 2/2005 | Heffelfinger | 356/446 |
| 6,856,446 B2 | 2/2005 | Di Carlo | 359/291 |
| 6,857,751 B2 | 2/2005 | Penn et al. | 353/97 |
| 6,870,660 B2 | 3/2005 | DiCarlo | 359/291 |

(Continued)

OTHER PUBLICATIONS

EP 1258288, Houston Univ.

(Continued)

*Primary Examiner* — Tu Nguyen

(74) *Attorney, Agent, or Firm* — James D. Welch

(57) ABSTRACT

Application of digital light processor (DLP) systems in an imaging ellipsometer or imaging polarimeter with a focusing means, sample and detector arranged to meet the Scheimpflug condition.

8 Claims, 9 Drawing Sheets

U.S. PATENT DOCUMENTS

| | | | | |
|---|---|---|---|---|
| 6,897,955 | B2 | 5/2005 | Wielsch | 356/369 |
| 6,906,687 | B2 | 6/2005 | Werner | 345/8 |
| 6,979,830 | B2 * | 12/2005 | Dietz et al. | 250/485.1 |
| 7,002,739 | B2 * | 2/2006 | Awamura | 359/385 |
| 7,006,995 | B1 | 2/2006 | Edenson et al. | 705/51 |
| 7,011,415 | B2 | 3/2006 | DiCarlo et al. | 353/99 |
| 7,019,881 | B2 | 3/2006 | Doherty et al. | 359/249 |
| 7,061,512 | B2 | 6/2006 | Morgan et al. | 345/691 |
| 7,072,094 | B2 | 7/2006 | Mezenner | 359/290 |
| 7,075,643 | B2 | 7/2006 | Holub | 356/326 |
| 7,088,486 | B2 | 8/2006 | DiCarlo | 359/224 |
| 7,095,498 | B2 | 8/2006 | Horie et al. | 356/364 |
| 7,116,459 | B2 | 10/2006 | Huffman | 359/239 |
| 7,126,682 | B2 | 10/2006 | Rowe et al. | 356/310 |
| 7,149,027 | B2 | 12/2006 | Mehrl | 359/290 |
| 7,158,180 | B2 | 1/2007 | Neidrich | 348/340 |
| 7,164,397 | B2 | 1/2007 | Pettitt | 345/63 |
| 7,187,484 | B2 | 3/2007 | Mehrl | 359/290 |
| 7,194,169 | B2 | 3/2007 | Ikeda et al. | 385/115 |
| 7,196,740 | B2 | 3/2007 | Huibers | 348/744 |
| 7,233,427 | B2 | 6/2007 | Doherty et al. | 359/245 |
| 7,236,150 | B2 | 6/2007 | Hui | 345/87 |
| 7,245,375 | B2 | 7/2007 | Finarov | 356/364 |
| 7,252,395 | B2 | 8/2007 | DiCarlo et al. | 353/99 |
| 7,262,817 | B2 | 8/2007 | Huibers | 348/771 |
| 7,265,766 | B2 | 9/2007 | Kempf | 345/690 |
| 7,518,724 | B2 * | 4/2009 | Rassman et al. | 356/369 |
| 7,567,345 | B1 | 7/2009 | Liphardt et al. | 356/369 |
| 7,777,878 | B2 * | 8/2010 | Liphardt | 356/330 |
| 2001/0010843 | A1 | 8/2001 | Garner | |
| 2002/0024640 | A1 | 2/2002 | Ioka | |
| 2002/0041420 | A1 | 4/2002 | Garner | |
| 2002/0057431 | A1 | 5/2002 | Fateley et al. | |
| 2002/0081582 | A1 | 6/2002 | Gao | |
| 2002/0171834 | A1 | 11/2002 | Rowe et al. | |
| 2003/0003032 | A1 | 1/2003 | Garner | |
| 2003/0019852 | A1 | 1/2003 | Kaplan | |
| 2003/0020703 | A1 | 1/2003 | Holub | |
| 2003/0054388 | A1 | 3/2003 | Garner et al. | |
| 2003/0062802 | A1 | 4/2003 | Battaglin et al. | |
| 2003/0138363 | A1 | 7/2003 | Gao | |
| 2003/0143131 | A1 | 7/2003 | Gao | |
| 2003/0186427 | A1 | 10/2003 | Gao | |
| 2004/0023368 | A1 | 2/2004 | Gao | |
| 2004/0035690 | A1 | 2/2004 | Gulari | |
| 2004/0159641 | A1 | 8/2004 | Kaplan | |
| 2005/0001820 | A1 | 1/2005 | Lee | |
| 2005/0030328 | A1 | 2/2005 | Yamada et al. | |
| 2005/0030470 | A1 | 2/2005 | Kim et al. | |
| 2005/0079386 | A1 | 4/2005 | Brown | |
| 2005/0213092 | A1 | 9/2005 | MacKinnon | |
| 2005/0251230 | A1 | 11/2005 | MacKinnon et al. | |
| 2006/0019757 | A1 | 1/2006 | Brunetti | |
| 2006/0028718 | A1 | 2/2006 | Seel et al. | |
| 2006/0038188 | A1 | 2/2006 | Erchak et al. | |
| 2006/0134669 | A1 | 6/2006 | Casasanta et al. | |
| 2006/0197757 | A1 | 9/2006 | Holub | |
| 2006/0220562 | A1 | 10/2006 | Tsukamoto | |

OTHER PUBLICATIONS

EP 00916981, Max Plancle Gesellschaft zur Forderung.

* cited by examiner

APPLICATION OF DIGITAL LIGHT PROCESSOR IN IMAGING ELLIPSOMETER AND THE LIKE SYSTEMS

CROSS-REFERENCE TO RELATED APPLICATIONS

This Application is a CIP of Ser. No. 12/002,650 Filed Dec. 18, 2007 now U.S. Pat. No. 7,777,878, and there via Claims Benefit of Provisional Application Ser. No. 60/875,599 Filed Dec. 19, 2006.

TECHNICAL FIELD

The present invention relates imaging ellipsometer and polarimeter or the like systems, and more particularly to application of digital light processors (DLP) in such systems to image selected regions of a sample.

BACKGROUND

Spectrometers and monochromators are known which accept a beam of spectroscopic electromagnetic radiation and disperse it into a spatially expanded spectrum of wavelengths which are individually monitored. It is also known to direct a beam of electromagnetic radiation onto a surface area of a sample and then image electromagnetic radiation reflecting from different locations of the sample by an array of detectors, such as by use of an imaging ellipsometer or the like system. It is further known that chopping beams can provide benefits.

Further, Digital Light Processors (DLP) are known and have been applied to modulate homogeneous light applied thereto and generate images thereby, however, DLP's are not believed to have been applied to, for instance, process images projected thereonto, such as those produced by incident electromagnetic radiation reflecting from a sample in systems such as ellipsometers, polarimeters, reflectometers spectrophotometers or the like which typically apply detectors with a multiplicity of detector elements, such as charge coupled devices (CCD's).

U.S. Patents which have been identified are:
U.S. Pat. Nos. 7,126,682; 7,265,766; 7,262,817; 7,252,395; 7,236,150; 7,233,427; 7,196,740; 7,194,169; 7,187,484; 7,164,397; 7,158,180; 7,149,027; 7,116,459; 7,088,486; 7,075,643; 7,072,094; 7,061,512; 7,019,881; 7,011,415; 7,006,995; 6,975,629; 6,965,470; 6,691,194; 6,937,382; 6,930,983; 6,906,852; 6,906,687; 6,870,660; 6,857,751; 6,856,446; 6,842,549; 6,781,094; 6,758,571; 6,741,503; 6,665,110; 6,654,516; 6,619,804; 6,618,186; 6,583,921; 6,558,006; 6,496,477; 6,459,425; 6,398,389; 6,298,370; 6,275,271; 6,259,153; 6,200,646; 6,179,489; 6,163,363; 6,105,119; 6,061,049; 5,932,119; 5,909,559; 5,658,559; 5,658,063; 4,114,366.

Published US Applications which have been identified are:
US2005/001820; US2006/0220562; US2005/0079386; US2002/0024640; US2003/0143131; US2004/0023368; US2002/0081582; US2003/0138363; US2006/019757; US2004/0035690; US2003/0020703; US2006/0197757; US2004/0159641; US2003/0186427; US2003/0019852; US2002/0041420; US2003/0003032; US2001/0010843; US2005/0251230; US2005/0213092; US2006/0134669; US2002/0171834; US2003/0054388; US2006/0028718; US2003/062802; US2003/062802; US1999/041007; US2006/096310; US2005/030470; US2004/008115; US1999/010866; US1997/025177; US1999/063385; US2001/014460; US2005/030328; US2005/031292; US2002/084238.

Published Foreign Applications which have been identified are:
EP1070823; EP1258288; EP00916981. It is mentioned that the 981 EP Patent describes sequential spectrometer followed by an imager. The parent application Ser. No. 12/002,650, of this Application, Claims a sequential imager followed by an imager.

Finally, as described in U.S. Pat. No. 7,567,345 to Liphardt et al., (incorporated by reference herein), it is known to provide cameras which are designed so that the "Scheimpflug" condition is substantially met to enable providing an image to a film which is in focus over a large film area even though the source of the image is spatially distributed over varying distances from the camera lens. A similar condition can be achieved in reflectometer, ellipsometer, polarizer or the like systems. To meet this condition in use, the source of a beam of electromagnetic radiation is caused to direct a beam of electromagnetic radiation to or from a sample along an oblique angle of incidence. Said beam approaches said focusing means along a locus which is substantially perpendicular to the plane thereof and then passes through said focusing means and impinges upon a sample placed on said stage for supporting a sample, or a detector, at an angle of incidence ($\beta$) with respect to a normal to a surface of said sample.

What is new, novel and non-obvious is:
- to apply digital light processors (DLP) to the end that images corresponding to a sequential multiplicity of regions on a sample are imaged onto a DLP, which images are then sequentially monitored by at least one detector element, sequential output from which is then interpreted or as corresponding to the corresponding locations on a sample surface;
- to apply digital light processors (DLP) in systems such an imaging ellipsometer or imaging polarimeter and the like imaging systems;
- applying the Scheimpflug condition on the detector side of an imaged sample.

DISCLOSURE OF THE INVENTION

While the present Application is not focused thereon, understanding thereof can be enhanced by considering a scanning spectrometer or monochromater system, which sequentially comprises:
- an input aperture;
- a dispersing means for spatially separating different wavelengths in electromagnetic radiation;
- a digital light processor;
- an imaging means; and
- a selection from the group consisting of:
    - at least one detector element;
    - at least one optical fiber; and
    - an exit aperture.

Said digital light processor comprises an array of a multiplicity of microscopic mirrors, each said microscopic mirror being controllable to reflect incident electromagnetic radiation along at least two different loci. In use said input aperture is positioned to receive spectroscopic electromagnetic radiation and provide at least a portion thereof to said dispersing means, which dispersing means serves to disperse said wavelengths into a spatially expanded spectrum of wavelengths and direct them to said digital light processor such that different wavelengths impinge on different microscopic mirrors therein. At least one of said microscopic mirrors can be oriented to reflectively direct electromagnetic radiation of a wavelength incident thereupon into said at least one detector element or optical fiber, while other microscopic mirrors in said digital light processor are oriented to reflectively direct electromagnetic radiation, (eg. of other wavelengths), away from said at least one detector element or optical fiber. It is noted that where a detector element is present the system is applicable as a scanning spectrometer, and where an optical fiber is present the system is a monochromator system which can provide selected wavelengths to a distal end thereof.

It is noted that the scanning spectrometer or monochromator system can comprise an imaging means which is selected from the group consisting of:
  it is telecentric having an entrance and/or exit pupil at infinity; and
  it is non-telecentric;
which can be a mirror, a lens, a system of lenses or a system of mirrors or combinations of at least one mirror and at least one lens, said selection typically being fashioned to reduce aberations. Further, the dispersion means can be a concave grating such as a produced by a holographic process, or a flat grating or a prism or functional equivalent. When present, the exit aperture will typically direct electromagnetic radiation exiting therefrom to a means for detecting it. As regards the telecentric imaging means, it is noted that placing a source of electromagnetic radiation at its focal point causes collimated electromagnetic radiation to exit therefrom, and causing collimated electromagnetic radiation to enter thereinto results in its being focused at the focal point thereof.

It is also noted that said scanning spectrometer or monochromator system can provide that the rates at which different microscopic mirrors (MM) thereof operate are selected from the group consisting of:
  the duty cycles of all microscopic mirrors (MM) are the same;
  the duty cycles of different microscopic mirrors (MM) are different; and
  the duty cycles of different microscopic mirrors (MM) are selected so as to provide a more homogeneous intensity output;
where "duty cycle" refers to the relationship between "on" and "off" times during which electromagnetic radiation is directed toward and away from the at least one detector element; at least one optical fiber; or said exit aperture.

A method of scanning a multiplicity of wavelengths and providing them as a sequential output from at least one detector element, optical fiber or exit aperture, comprises the steps of:
  a) providing a system sequentially comprising:
    an input aperture;
    a dispersing means for spatially separating different wavelengths in electromagnetic radiation;
    a digital light processor;
    a imaging means for directing electromagnetic radiation; and
    a selection from the group of:
      at least one detector element;
      at least one optical fiber; and
      an exit aperture;
    said digital light processor comprising an array of a multiplicity of microscopic mirrors, each said microscopic mirror being controllable to reflect incident electromagnetic radiation along at least two different loci;
    such that in use said input aperture is positioned to receive spectroscopic electromagnetic radiation and provide at least a portion thereof to said dispersing means, which dispersing means serves to disperse said wavelengths into a spatially expanded spectrum of wavelengths and direct them to said digital light processor such that different wavelengths impinge on different microscopic mirrors, at least one of which microscopic mirrors is oriented to reflectively direct electromagnetic radiation of a wavelength incident thereupon into said at least one detector element, optical fiber or exit aperture, while other microscopic mirrors in said digital light processor are oriented to reflectively direct electromagnetic radiation, (eg. of other wavelengths), away from said at least one detector element, optical fiber or exit aperture;
  b) causing spectroscopic electromagnetic radiation to pass through said input aperture, impinge on said dispersing means, and reflect from said dispersing means as a dispersed spatially expanded spectrum of wavelengths, such that different wavelengths impinge on different microscopic mirrors in said digital light processor;
  c) causing at least one microscopic mirror in said digital light processor to be oriented to reflectively direct electromagnetic radiation of a first wavelength, which impinges thereupon, into said at least one detector element, optical fiber or exit aperture while reflectively directing electromagnetic radiation incident on other microscopic mirrors away from said at least one detector element, optical fiber or exit aperture;
  d) causing the microscopic mirror oriented to reflectively direct electromagnetic which impinges thereupon into said at least one detector element, optical fiber or exit aperture in step c, to become reoriented so that electromagnetic which impinges thereupon is redirected so that it does not enter said at least one detector element, optical fiber or exit aperture, along with causing at least one other microscopic mirror in said digital light processor to be oriented to reflectively direct electromagnetic radiation of another wavelength, which impinges thereupon, into said at least one detector element or optical fiber while reflectively directing electromagnetic radiation incident on other microscopic mirrors away from said at least one detector element, optical fiber or exit aperture; and
monitoring the sequential output of said at least one detector element, optical fiber or exit aperture as the orientations of said microscopic mirrors are changed and interpreting said output as a sequence of different wavelengths.

In the foregoing it is important to realize that while use thereof is not prohibited, no multiple element detector such as a charge coupled device (CCD) is necessary. A single detector element can be applied to sequentially monitor electromagnetic radiation directed thereinto by a Digital Light Processor.

The present invention specifically does comprise an imaging system, such as an imaging ellipsometer or imaging polarimeter or the like system, sequentially comprising:
  a source of electromagnetic radiation;
  a collecting means for directing electromagnetic radiation, (eg. a collimating lens);
  a stage for supporting a sample;
  a first focusing means, (eg. a lens);
  a digital light processor;
  a second focusing means, (eg. a lens);
  a detector element; and
  said imaging system further comprising polarization state generation and polarization state analysis means between said source of electromagnetic radiation and said sample, and between said sample and said at least one detector element, respectively;
Said digital light processor comprising an array of a multiplicity of microscopic mirrors, each said microscopic mirror being controllable to reflect incident electromagnetic radiation along at least two different loci. In use said source of electromagnetic radiation provides an expanding beam of electromagnetic radiation to said collecting means, which in turn directs electromagnetic radiation onto a sample placed on said stage for supporting a sample; and such that said first focusing means focuses collected electromagnetic radiation reflecting from said sample. At least one of said microscopic mirrors in said digital light processor is caused to be oriented to direct electromagnetic radiation incident thereupon to said second focusing means, which in turn focuses electromagnetic radiation provided thereto from said at least one microscopic mirror, onto said at detector element.

It is noted that the detector element can be one element of a multiple element detector, or can comprise a light fiber or exit aperture.

A modified imaging system, (wherein said digital light processor is a first digital light processor); which further comprises, between said first digital light processor and said at least one detector element, a spectrometer sequentially comprising:
    a dispersing means, (eg. a grating), for spatially separating different wavelengths in electromagnetic radiation; and
    a second digital light processor;
such that said dispersing means receives electromagnetic radiation from said first digital light processor and directs it to said dispersing means which provides electromagnetic radiation to said second digital light processor and directs it to said at least one detector element.

A present invention method of imaging a sample and providing said image as a sequential output from a detector element, comprises the steps of:
  a) providing an imaging system as just described;
  b) causing said source of electromagnetic radiation to provide an expanding beam of electromagnetic radiation to said collecting means, which in turn directs electromagnetic radiation onto a sample placed on said stage for supporting a sample; and causing said first focusing means to focus collected electromagnetic radiation reflecting from said sample;
  c) causing at least one of said microscopic mirrors in said digital light processor to be oriented to direct electromagnetic radiation incident thereupon to said second focusing means, which in turn focuses electromagnetic radiation provided thereto from said at least one microscopic mirror onto said detector element.

Said method can further comprise:
  d) causing said at least one microscopic mirror in said digital light processor which was caused to be oriented to direct electromagnetic radiation incident thereupon to said second focusing means in step c, to be reoriented so as to direct incident electromagnetic radiation away from said detector element; and causing at least one other microscopic mirror in said digital light processor to be oriented to direct electromagnetic radiation incident thereupon to said second focusing means which in turn focuses electromagnetic radiation provided thereto from said at least one microscopic mirror onto said detector element, which in turn focuses electromagnetic radiation provided thereto from said at least one microscopic mirror onto said detector element;
monitoring the sequential output of said detector element as the orientations of said microscopic mirrors are changed and interpreting said output as a sequence of images of different locations on said sample.

Said method can also comprise combining data obtained by practice of steps a-d to provide a composite image.

In the foregoing it is important to realize that no multiple element detector such as a charge coupled device (CCD) is necessary. A single detector element can sequentially monitor electromagnetic radiation directed thereinto by a operation of a digital light processor. It is also noted that if electromagnetic radiation reflected by a digital light processor mirror is spectroscopic, it is possible to spatially disperse the wavelengths, such as by applying the electromagnetic radiation to a diffraction dispersing means or functional equivalent, and sequentially or simultaneously direct different wavelengths to different single element detectors.

It is also disclosed that another method, enables providing a beam of relatively uniform intensity over a wide range of wavelengths, and comprises the steps of:
  a) providing a system comprising:
    a source of spectroscopic electromagnetic radiation having a non-uniform intensity vs. wavelength characteristic;
    a dispersion means; and
    a digital light processor;
said digital light processor comprising an array of a multiplicity of microscopic mirrors, each said microscopic mirror being controllable to reflect incident electromagnetic radiation along at least two different loci;
  b) causing said source of spectroscopic electromagnetic radiation having a non-uniform intensity vs. wavelength characteristic to impinge on said dispersion means and exit therefrom as a spectrum of spatially separated wavelengths which are directed to impinge on said digital light processor;
  c) causing microscopic mirrors in said digital light processor to be oriented such that more thereof receiving wavelengths having a relatively low intensity direct electromagnetic radiation incident thereon to a detector, while less thereof are oriented to direct wavelengths having a relatively high intensity are so directed.

It is mentioned that a method of providing a chopped beam comprises the steps of:
  a) providing a source of a beam of electromagnetic radiation and a digital light processor comprising an array of a multiplicity of microscopic mirrors, each said microscopic mirror being controllable to reflect incident electromagnetic radiation along at least two different loci;
  b) causing said source to provide a beam directed to impinge on said digital light processor and monitoring a beam reflected therefrom which causing at least some of said microscopic mirrors to quickly change orientation.

Chopped beams are beneficial as, for instance, they can be detected with better stability, and can be used in lighted rooms using a demodulation technique.

It is also noted that not all microscopic mirrors have to be quickly changed at the same rapid changing rate. For instance, an apodizing filter can be approximated by causing microscopic mirrors that reflect the outer perimeter of a beam at a different rate than are microscopic mirrors in the more central regions. This can, for instance, cause more or less overall intensity to reflect from the periphery of the beam than from the more central regions via duty cycling.

It is to be understood that any of the foregoing Methods can also involve obtaining data by application of a data detector, and performing at least one selection from the group consisting of:
  storing at least some data provided by said data detector in machine readable media;
  analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

It is also noted that a present invention imaging ellipsometer or polarimeter system can beneficially orient the focusing means (L1), sample (S) and digital light processor (DLP) system to meet the Scheimpflug condition. This likewise applies to practice of the present invention methodology.

Further, it is to be understood that those skilled in the relevant art agree that electromagnetic radiation is altered in a concrete and tangible way by interaction with, (eg. by reflecting from and/or transmitting through), a material system. This can be, for instance, at the quantum level and/or effects on intensity and/or beam polarization state, which are be changed thereby.

Finally, as is better described in the Detailed Description Section in conjunction with FIGS. 5a and 5b, the present invention includes methodology involving use of a system configured to meet the Scheimpflug condition.

The invention will be better understood by reference to the Detailed Description Section, in combination with the Drawings.

DETAILED DESCRIPTION

Figure 1A:
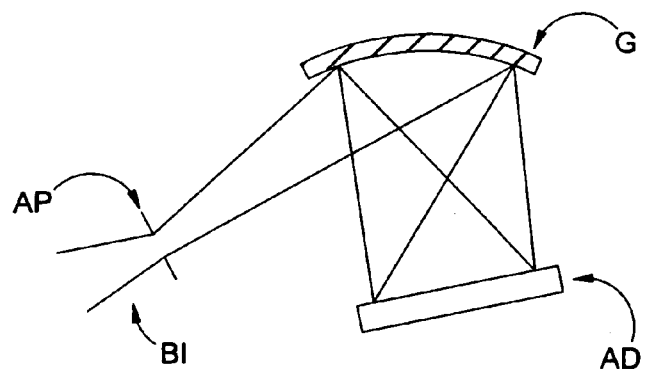
FIG. 1a shows a Prior Art Spectrometer.

Turning now to the Drawings, FIG. 1a shows a Prior Art Spectrometer comprised of an Input Aperture (AP), a Grating (G) and an Array Detector (AD) such as a CCD array.

Figure 1B:
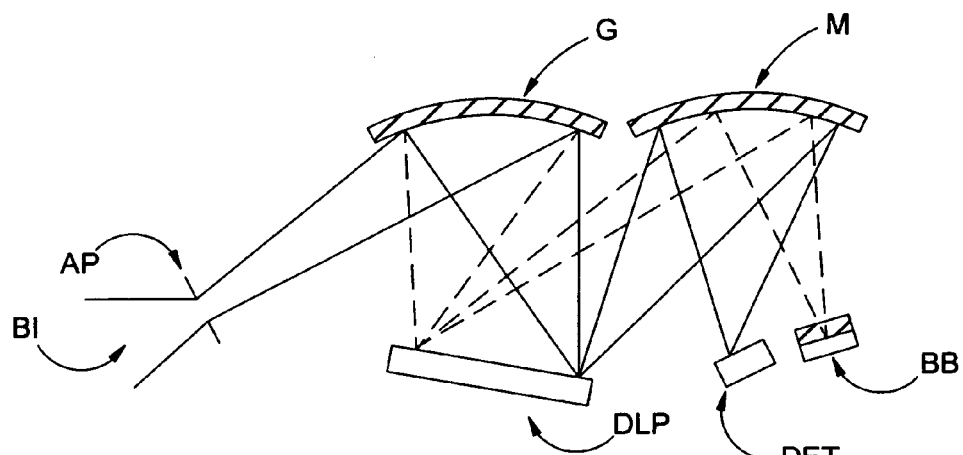
FIG. 1b shows a Present Invention Scanning Spectrometer System.

FIG. 1b shows a Present Invention Scanning Spectrometer System sequentially comprising:
an Input Aperture (AP);
a Dispersing Means (G) for spatially separating different wavelengths in electromagnetic radiation;
a Digital Light Processor (DLP);
an Imaging Means (M) for directing electromagnetic radiation; and
at least one Detector Element (DET).

Note that the at least one Detector Element (DET) can be a selection from the group consisting of:
said at least one Detector Element (DET);
at least one Optical Fiber (OF); and
an Exit Aperture (EA).

Note, if the at least one Detector (DET) Element is replaced by at least one Optical Fiber, FIG. 1b can be considered an Monochromator that provides selected wavelengths at a distal end thereof.

Figure 1C:
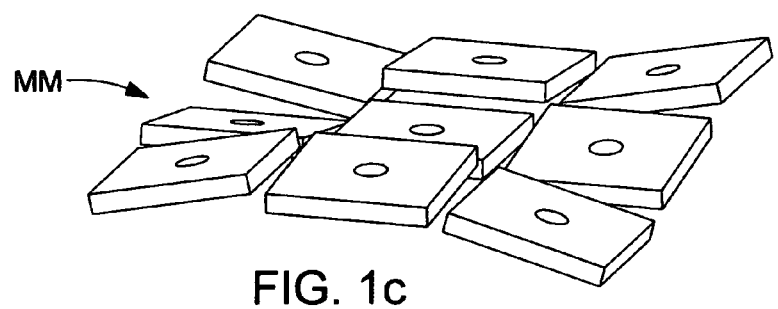
FIG. 1c shows nine elements of a Texas Instruments Digital Light Processor (DLP) system, in various states.

It is noted that said Digital Light Processor (DLP) comprises an array of a multiplicity of Microscopic Mirrors (MM), (see FIG. 1c), each said Microscopic Mirror being controllable to reflect incident electromagnetic radiation along at least two different loci. FIG. 1c is shows nine elements of a Texas Instruments, (Trademark), Digital Light Processor (DLP) system in various states.

Returning to FIG. 1b it should be appreciated that in use said Input Aperture (AP) is positioned to receive Spectroscopic Electromagnetic Radiation (BI) and provide at least a portion thereof to said Dispersing Means (G), (eg. a Concave Grating), which Dispersing Means (G) serves to disperse said wavelengths into a spatially expanded spectrum of wavelengths and direct them to said Digital Light Processor (DLP) such that different wavelengths impinge on different Microscopic Mirrors (MM) therein. At least one of said Microscopic Mirrors (MM) is then oriented to reflectively direct electromagnetic radiation of a wavelength incident thereupon toward said Imaging Means (M) which directs it into said Detector Element (DET). Other Microscopic Mirrors (MM) in said Digital Light Processor (DLP) are oriented to reflectively direct electromagnetic radiation, (eg. of other wavelengths), away from said Detector Element (DET).

Figure 2A:
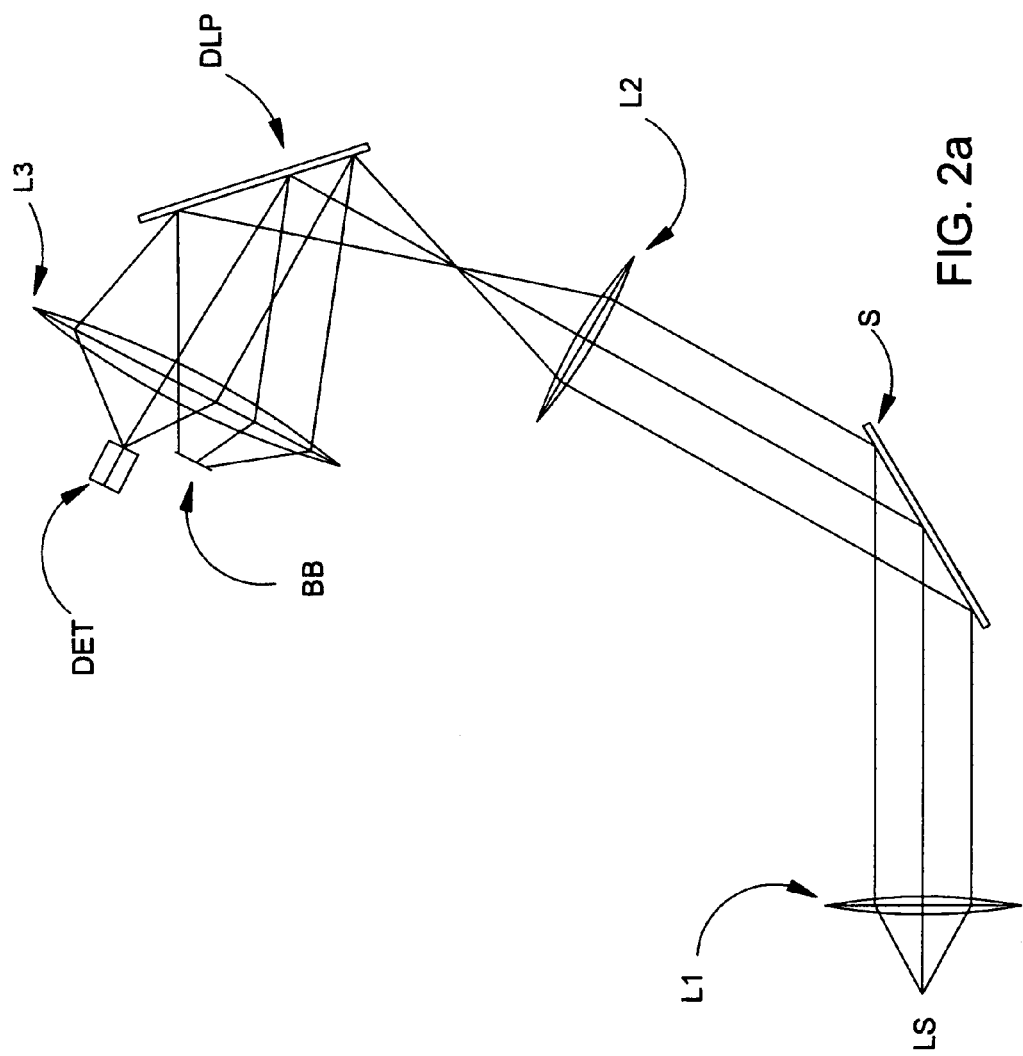
FIG. 2a shows a Present Invention Imaging Ellipsometer or the like system with more than one microscopic mirror (MM) directing electromagnetic radiation directed to a detector element (DET).

FIG. 2a shows a Present Invention Imaging System such as an imaging ellipsometer, an imaging polarimeter, an imaging reflectometer, and imaging spectrophotometer or the like system, sequentially comprising:
a Source (LS) of electromagnetic radiation;
a Collecting Means (L1);
a Stage (STG) for supporting a Sample (S);
a First Focusing Means (L2);
a Digital Light Processor (DLP);
a Second Focusing Means (L3); and
at least one Detector Element (DET).
said imaging system further optionally comprising Polarization State Generation (PSG) and Polarization State Analysis (PSA) means between said source of electromagnetic radiation and said sample, and between said sample and said at least one detector element, respectively.

Figure 2B:
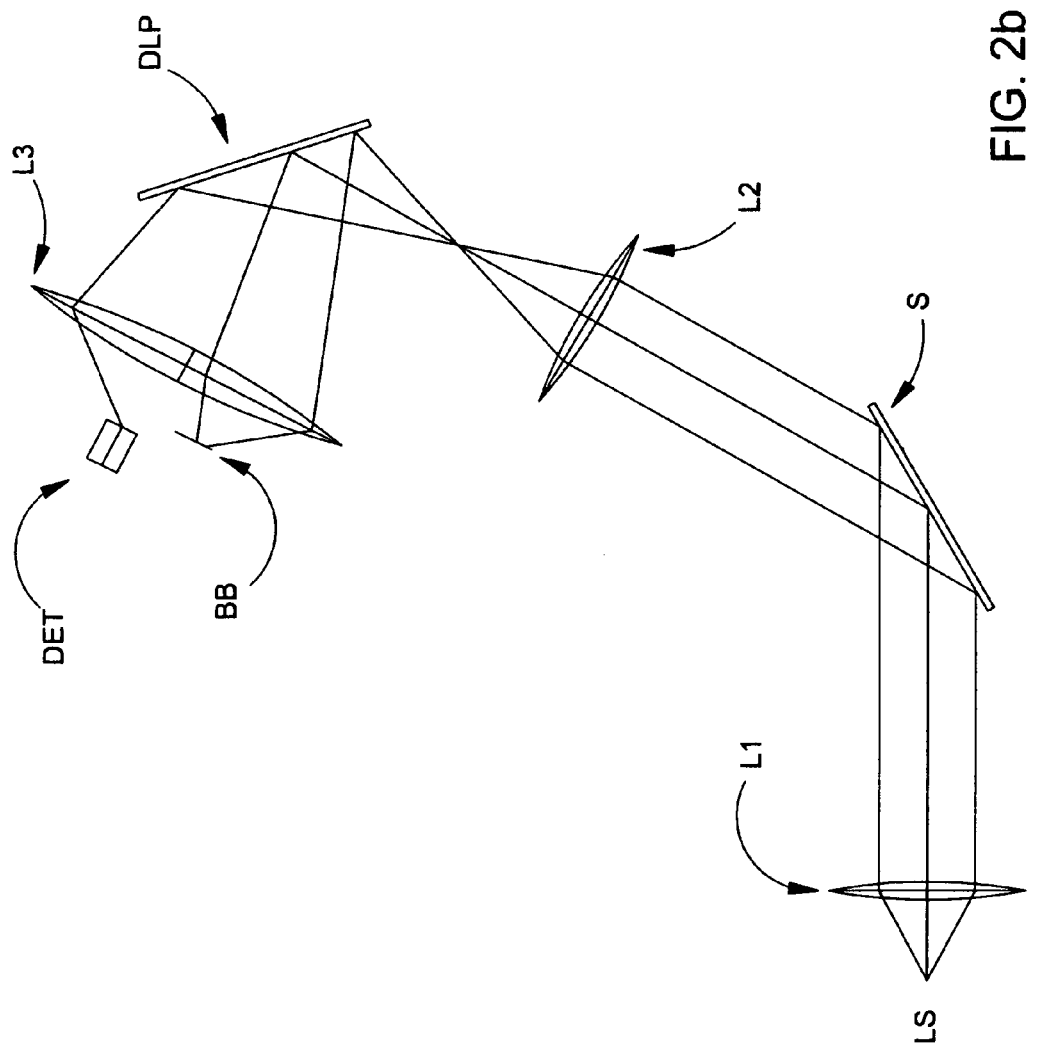
FIG. 2b shows FIG. 2a with one microscopic mirror (MM) directing electromagnetic radiation directed to a detector element (DET) and with other microscopic mirrors (MM) directing electromagentic radiation to a beam block (BB).

Note that multiple (DLP) Microscopic Mirrors (MM) direct electromagentic radiation to the detector (DET) in FIG. 2a. FIG. 2b is included to show FIG. 2a with only one Microscopic Mirror (MM) directing electromagnetic radiation directed to a detector element and with other microscopic mirrors directing electromagentic radiation to a Beam Block (BB). This is important in imaging applications where data from a single location on a sample is desired.

Figure 4A:
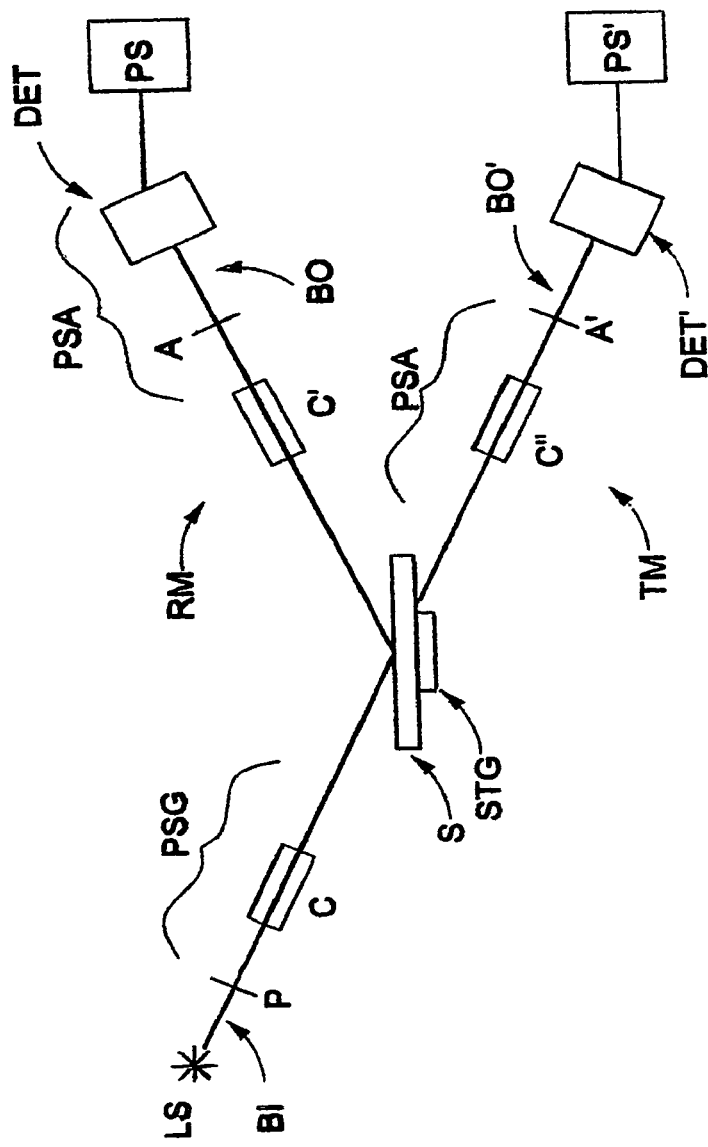
FIG. 4a demonstrates an ellipsometer system for general disclosure.

As demonstrated in FIG. 4a, said (PSG) can comprise a Polarizing Element (P), optionally in combination with a Compensator (C), and the (PSA) can comprise an Analyzing Element (P), optionally in combination with a Compensator (C') (C'').

As described above, said Digital Light Processor (DLP) comprises an array of a multiplicity of Microscopic Mirrors (MM) as demonstrated in FIG. 1c. Again, each said Microscopic Mirror (MM) is controllable to reflect incident electromagnetic radiation along at least two different loci.

Returning to FIGS. 2a and 2b, in use said Source (LS) of electromagnetic radiation provides an expanding beam of electromagnetic radiation (BI) to said Collecting Means (L1), which in turn directs electromagnetic radiation onto a Sample (S) placed on said stage for supporting a sample. Said First Focusing Lens (L2) focuses collected electromagnetic radiation reflecting from said Sample (S) to a point (FP) between said First Focusing Lens (L2) and said Digital Light Processor (DLP) such that electromagnetic radiation impinges on said Digital Light Processor (DLP) as an expanding beam. At least one of said Microscopic Mirrors (MM) in said Digital Light Processor (DLP) is caused to be oriented to direct electromagnetic radiation incident thereupon to said Second Focusing Means (L3), which in turn focuses electromagnetic radiation provided thereto from said at least one Microscopic Mirror (MM) onto said at least one Detector Element (DET). Note that other of said Digital Light Processor (DLP) Microscopic Mirrors (MM) are simultaneously set to direct electromagnetic radiation away from said at least one Detector Element (DET), and optionally at an absorbing Beam Block Means (BB) which serves to absorb and prevent stray electromagnetic radiation from entering said at least one Detector Element (DET). Note that the focus point of (L2) can be between said First Focusing Means (L2) and the Digital Light Processor (DLP) so that the beam is expanding as it approaches the later.

Figure 2C:
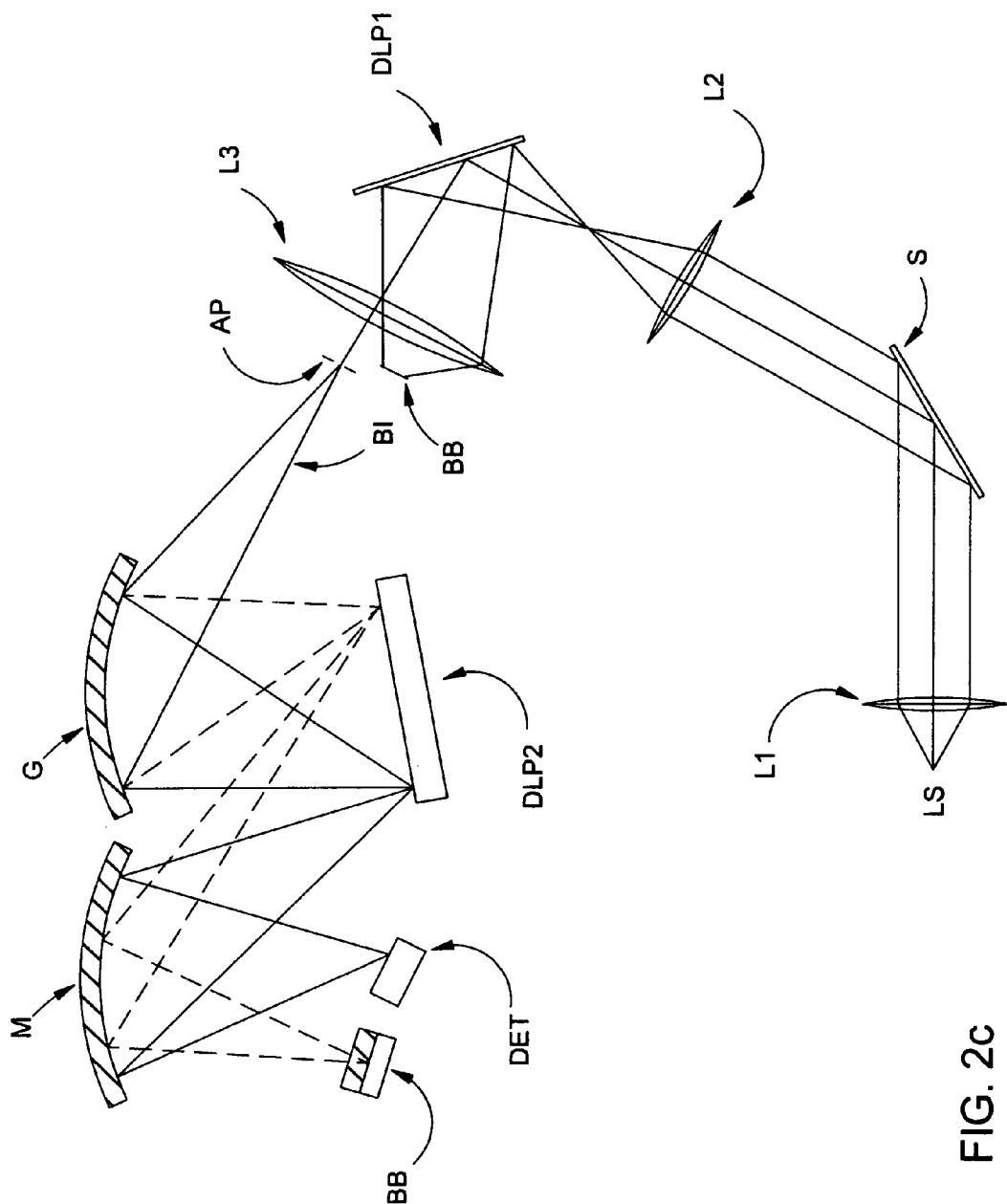
FIG. 2c shows a Present Invention Imaging Ellipsometer or the like system combined with a Scanning Spectrometer System.

FIG. 2c shows the system of FIGS. 2a and 2b, combined with the Wavelength Scanning system of FIG. 1b. This combination is useful in monitoring the wavelength spectrum of electromagnetic radiation reflected from specific Digital Light Processor (DLP) Microscopic Mirrors (MM), which monitor a specific location on a Sample (S). The same identifiers used in FIGS. 2a and 1b are applicable in FIG. 2c.

Figure 3A:
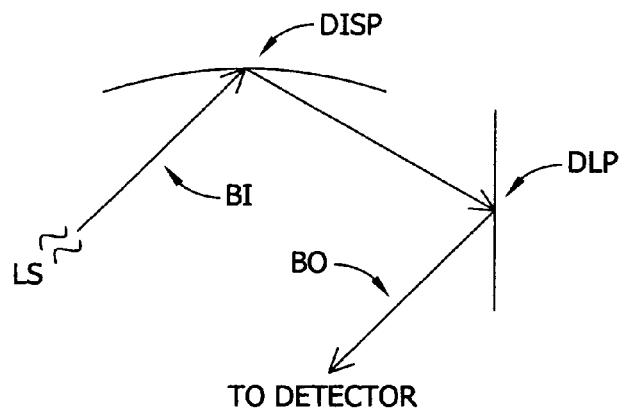
FIGS. 3a and 3b show a system for providing a beam of electromagnetic radiation having a relatively uniform intensity over a wide range of wavelengths.
Figure 3B:
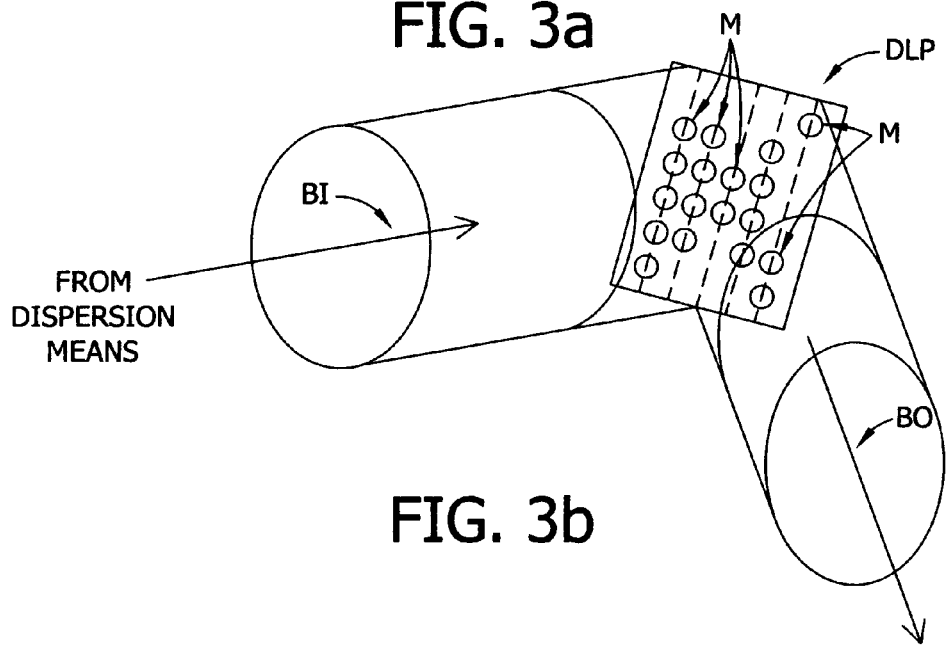
Figure 3C:
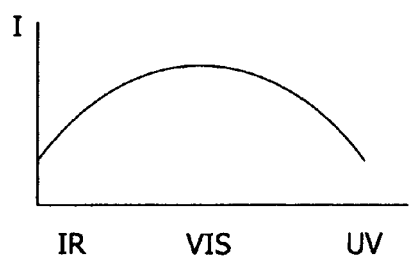
FIGS. 3c and 3d show plots of intensity vs. wavelength spectrum of the Source (LS) and a spectrum exiting the (DLP) possible using the system of FIGS. 3a and 3b.
Figure 3D:
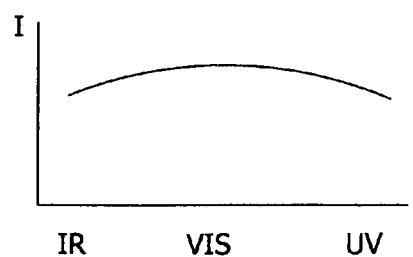

FIGS. 3a and 3b show a system for providing a beam of electromagnetic radiation having a relatively uniform intensity over a wide range of wavelengths. FIG. 3a shows a Spectroscopic Source (LS) of a beam of electromagnetic radiation (BI) which is directed to a Dispersion means (DISP). Electromagnetic radiation exiting said Dispersion means (DISP) is characterized by having a spatially separated wavelength spectrum. Said dispersed wavelengths are directed to a Digital Light Processor (DLP), in which Microscopic Mirrors (MM) thereof are operated so that so that those receiving wavelengths of relatively low intensity reflect wavelengths toward a Detector (DET) at a duty cycle with a relatively longer "on" than "off" duty cycle than do said Microscopic Mirrors (MM) which receive wavelengths of a higher intensity. FIG. 3b shows less Microscopic Mirrors (M) in a central region of the (DLP) are oriented to direct impinging electromagnetic radiation (BI) toward a Detector as (BO) than are Microscopic Mirrors (M) at the sides of the (DLP). This configuration would be beneficial where, for instance, the central portion of the (DLP) received Visible wavelengths and the laterally positioned Microscopic Mirrors (M) received (IR) and (UV) wavelengths and the Source (LS) provided higher intensity Visible (VIS) wavelengths and lower intensity Infrared (IR) and Ultraviolet (UV) wavelengths. FIGS. 3c and 3d show exemplary plots of Intensity vs. Wavelength to demonstrate the effect. FIG. 3c demonstrate the spectrum of the Source (LS) provided electromagnetic radiation (BI) and FIG. 3d a spectrum of electromagnetic radiation (BO) exiting the (DLP).

FIG. 4a is included to generally disclose a representative ellipsometer system. Note that a Source (LS) of electromagnetic radiation provides a beam (BI) of electromagnetic radiation which passes through a Polarizer (P) and Compensator (C) before interacting with a Sample either by reflection (RM) or transmission (TM). Said reflection mode (RM) beam is shown to pass through a Compensator (C') and an Analyzer (A) then enter a Detector (DET) as beam (BO), which can produce a signal and provide it to some system for producing a concrete and tangible result (PS). The transmission mode (TM) beam likewise is shown to pass through a Compensator (C'') and an Analyzer (A') then enter a Detector (DET') as beam (BO'), which can produce a signal and provide it to some system for producing a concrete and tangible result (PS'). It is to be appreciated that the Polarizer (P) can independently, or in combination with the Compensator (C), comprise a Polarization State Generator (PSG). Likewise the Analyzer (A) (A') can independently, or in combination with the Compensator (C') (C''), comprise a Polarization State Analyzer (PSA). A present invention imaging ellipsometer has the Digital Light Processor (DLP) included as alluded to above.

Figure 4B:
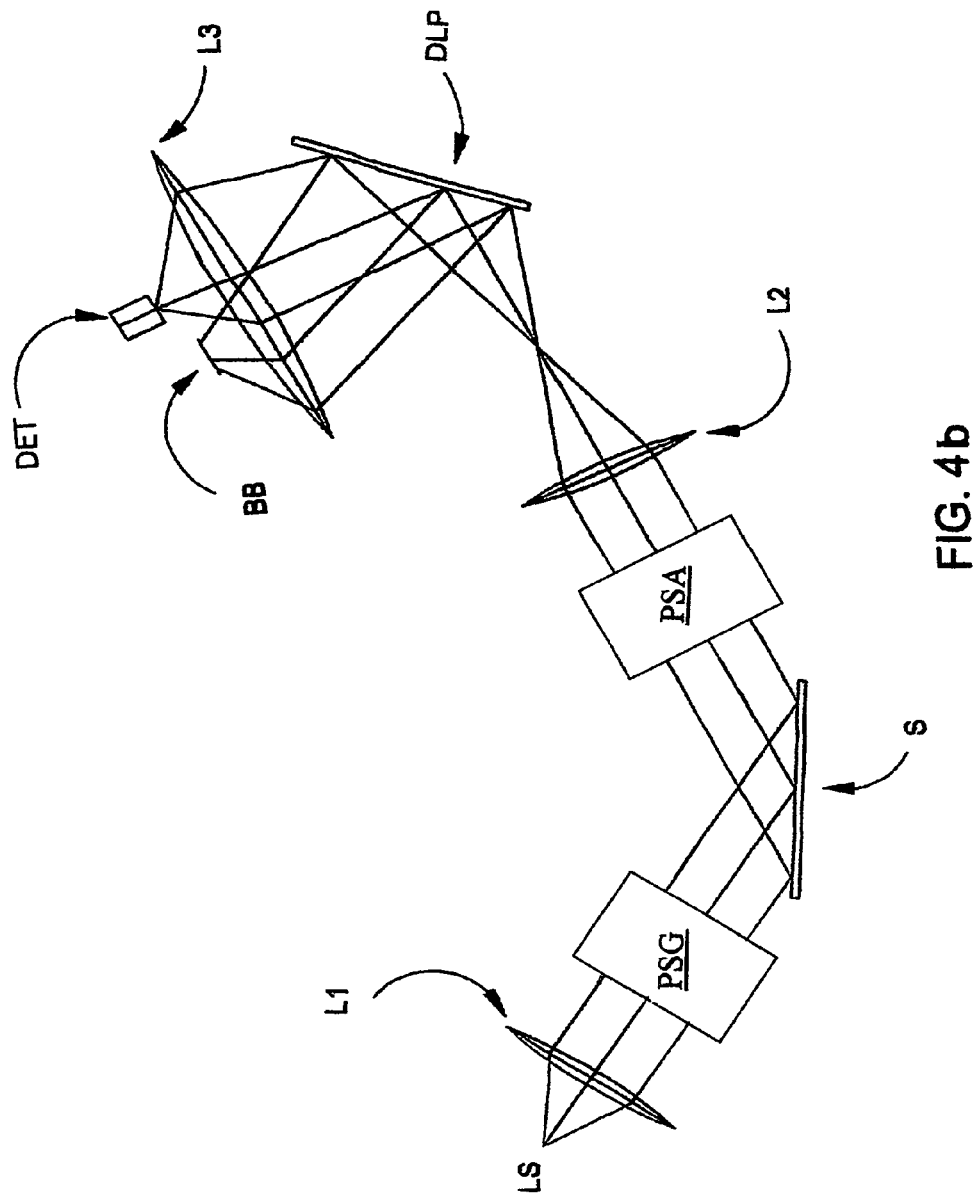
FIG. 4b demonstrates a present invention imaging ellipsometer system.

FIG. 4b demonstrates a present invention imaging ellipsometer system. It is essentially the system of FIG. 2b with Polarization State Generator (PSG) and Polarization State Analyzer (PSA) added prior to and after, respectively, the Sample (S) which is imaged. As for the system in FIG. 2b, said Source (LS) of electromagnetic radiation provides an expanding beam of electromagnetic radiation (BI) to said Collecting Means (L1), which in turn directs electromagnetic radiation onto a Sample (S) placed on said stage for supporting a sample. Said First Focusing Lens (L2) focuses collected electromagnetic radiation reflecting from said Sample (S) to a point (FP) between said First Focusing Lens (L2) and said Digital Light Processor (DLP) such that electromagnetic radiation impinges on said Digital Light Processor (DLP) as an expanding beam. At least one of said Microscopic Mirrors (MM) in said Digital Light Processor (DLP) is caused to be oriented to direct electromagnetic radiation incident thereupon to said Second Focusing Means (L3), which in turn focuses electromagnetic radiation provided thereto from said at least one Microscopic Mirror (MM) onto said at least one Detector Element (DET). Note that other of said Digital Light Processor (DLP) Microscopic Mirrors (MM) are simultaneously set to direct electromagnetic radiation away from said at least one Detector Element (DET), and optionally at an absorbing Beam Block Means (BB) which serves to absorb and prevent stray electromagnetic radiation from entering said at least one Detector Element (DET). Note that the focus point of (L2) can be between said First Focusing Means (L2) and the Digital Light Processor (DLP) so that the beam is expanding as it approaches the later. What is different is that a polarization state is imposed in the collimated beam of electromagnetic radiation between the Collecting Means (L1) and the Sample (S), and the polarization state of the beam after reflecting from the Sample (S) is analyzed before entering said First Focusing Means (L2).

Figure 5A:
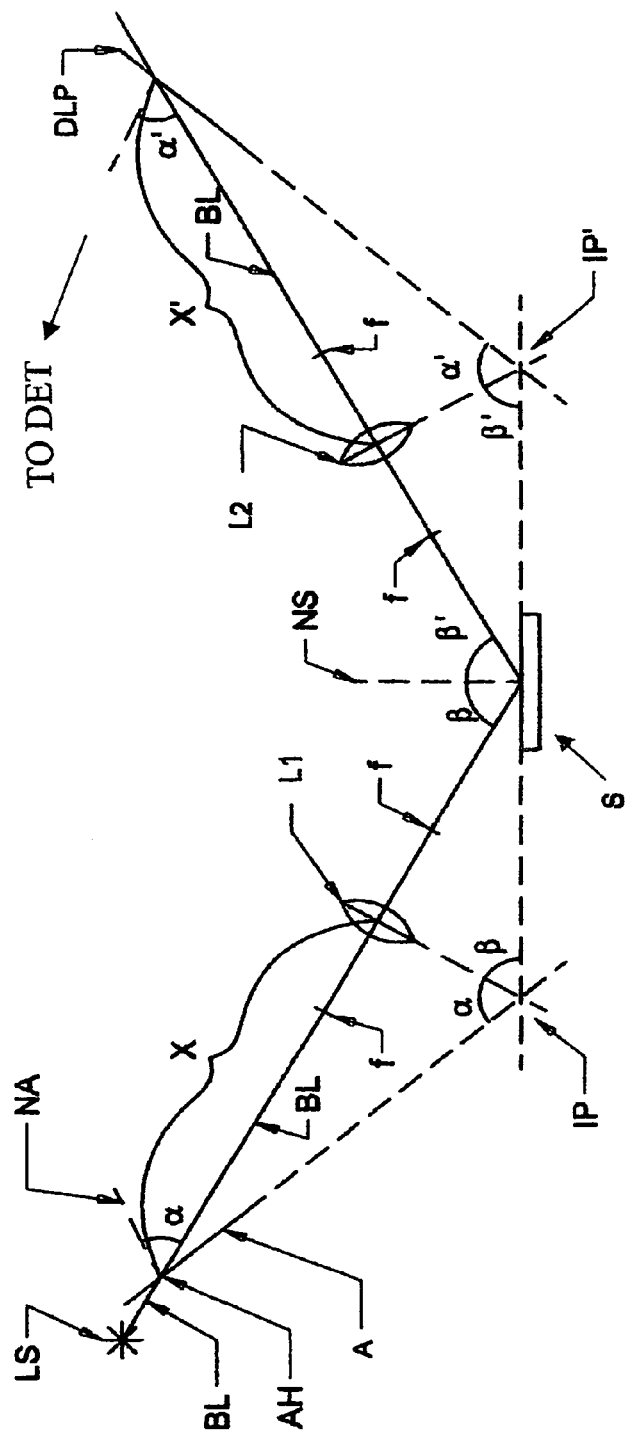
FIGS. 5a and 5b demonstrate the "Scheimpflug" condition.
Figure 5B:
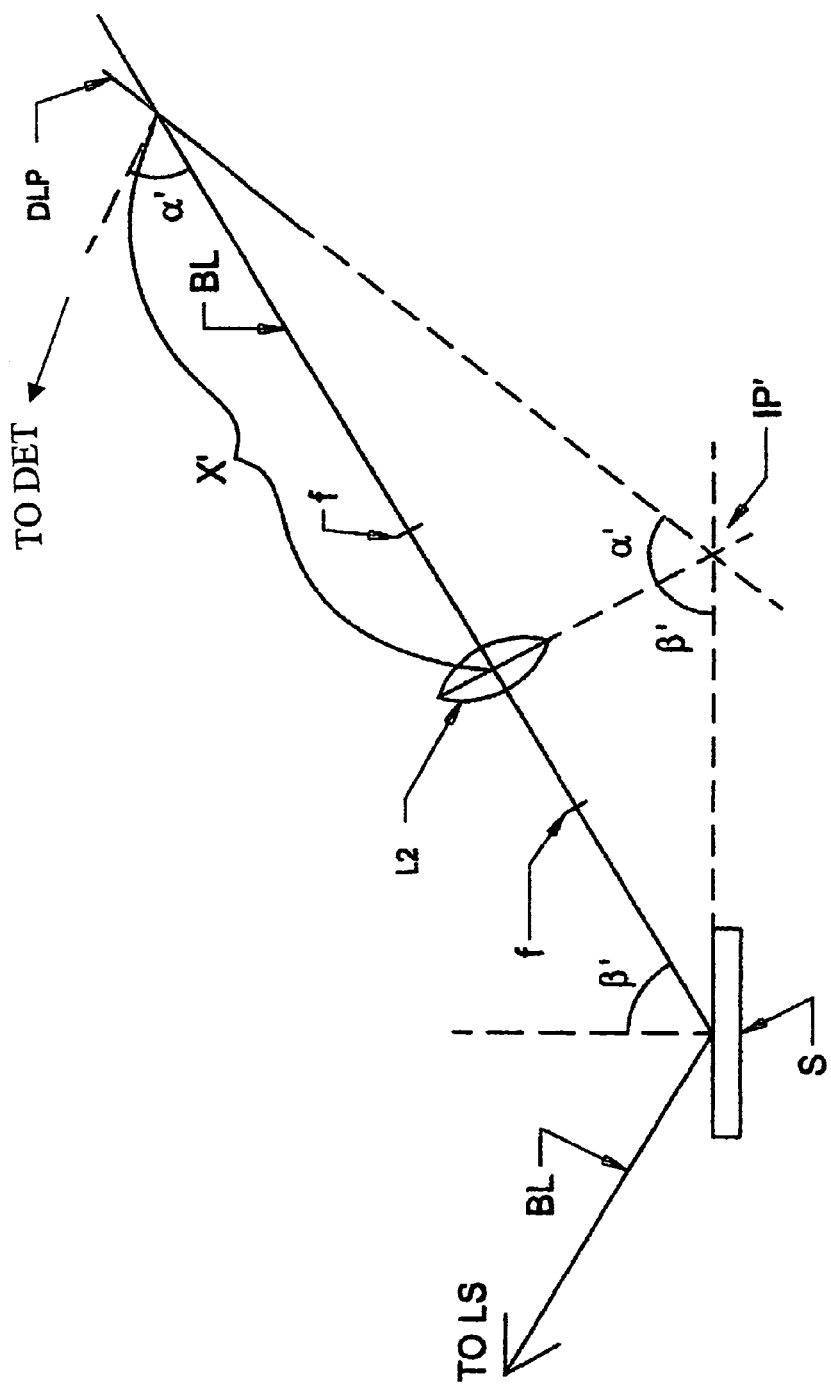

Turning now to FIGS. 5a and 5b, there is shown in FIG. 5a relative positioning and orientation of the locus of a Beam of electromagnetic radiation (BL) from a Source (LS) thereof, and a projected normal (NA) to the plane of the Aperture (A), a Focusing Means (L1), (eg. lens), and a Sample (S) and a mathematical relationship defined by the "Scheimpflug" condition. Note the location of the identified elements and how the angles ($\alpha$) and ($\beta$) are defined. In particular, Alpha ($\alpha$) is the angle between the Beam (BL) and a normal to the plane of the Aperture (A), and Beta ($\beta$) is the oblique angle between said Beam (BL) and a normal to the plane of the Sample (S). The Equation shown is the defining equation for the Scheimpflug condition:

$$\mathrm{Tan}(\alpha) = (X-f)/f\,\mathrm{Tan}(\beta);$$

where "X" is the distance from the aperture, at the point at which said beam passes therethrough, to a center of said focusing means, and "f" is the focal length of said focusing means. Again, Alpha ($\alpha$) is the angle of rotation of the Perpendicular to the plane of the Aperture (A) with respect to the Beam (BL), and Beta ($\beta$) is the oblique angle of incidence of the beam on the Sample (S) surface. Note that projected planes of the Aperture (A), Focusing Means (L1) and Sample (S) intersect at Intersection Point (IP) when the Scheimpflug condition is substantially met.

FIG. 5a also shows the "Scheimpflug" condition, as demonstrated on the Detector side of a Sample (S). Note that the planes of the Sample (S), Detector (D) and Focusing Means (L2) intersect along a line at (IP'). FIG. 5b shows a system wherein the "Scheimpflug" condition is met specifically on Detector side of a Sample (S).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. An imaging ellipsometer or polarimeter system sequentially comprising, in the following order:
    a source (LS) of electromagnetic radiation;
    a collecting means (L1) for directing electromagnetic radiation;
    a stage (STG) for supporting a sample (S);
    a first focusing means (L2);
    a digital light processor (DLP);
    a second focusing means (L3); and
    at least one detector element (DET);
    said imaging system further comprising polarization state generation (PSG) and polarization state analysis (PSA) means between said source of electromagnetic radiation and said sample, and between said sample and said at least one detector element, respectively;
said digital light processor (DLP) comprising an array of a multiplicity of microscopic mirrors (MM), each said microscopic mirror (MM) being controllable to reflect incident electromagnetic radiation along at least two different loci;
said collecting means, first focusing means and second focusing means all being selected from the group consisting of:
    a lens;
    a mirror;
    a system of lenses;
    a system of mirrors;
    a system comprising at least one lens and at least one mirror;
such that in use said source (LS) of electromagnetic radiation provides an expanding beam (BI) of electromagnetic radiation to said collecting means (L1), which in turn directs electromagnetic radiation onto a sample (S) placed on said stage (STG) for supporting a sample (S); and such that said first focusing means (L2) generates an image of said sample (S) on said digital light processor (DLP); at least one of said microscopic mirrors (MM) in said digital light processor (DLP) being caused to be oriented to direct electromagnetic radiation incident thereupon to said second focusing means (L3), which in turn focuses electromagnetic radiation provided thereto from said at least one microscopic mirror (MM) onto said at least one detector element (DET) while other of said microscopic mirrors (MM) direct electromagnetic radiation away therefrom.

2. An imaging system as in claim 1 which further comprises, between said digital light processor (DLP) and said at least one detector element (DET), a spectrometer sequentially comprising:
    a dispersing means (G) for spatially separating different wavelengths in electromagnetic radiation; and
    a second digital light processor (DLP2);
and wherein said digital light processor (DLP) is a first digital light processor;
such that said dispersing means (G) receives electromagnetic radiation from said first digital light processor (DLP) and directs it to said dispersing means (G) which provides electromagnetic radiation to said second digital light processor (DLP2) and directs it to said at least one detector element (DET).

3. An imaging system as in claim 1 in which the detector comprises a single detector element (DET) which sequentially monitors sample images directed thereto.

4. An imaging ellipsometer or polarimeter system as in claim 1 in which the sample (S) and digital light processor (DLP) system and first focusing means (L2) are oriented to meet the Scheimpflug condition.

5. A method of imaging a sample and providing said image as a sequential output from a detector element, comprising the steps of:
    a) providing an imaging system sequentially comprising:
        a source (LS) of electromagnetic radiation;
        a collecting means (L1) for directing electromagnetic radiation;
        a stage (STG) for supporting a sample (S);
        a first focusing means (L2);
        a digital light processor (DLP);
        a second focusing means (L3); and
        at least one detector element (DET);
        said imaging system further comprising polarization state generation (PSG) and polarization state analysis (PSA) means between said source of electromagnetic radiation and said sample, and between said sample and said at least one detector element, respectively;
        said digital light processor (DLP) comprising an array of a multiplicity of microscopic mirrors (MM), each said microscopic mirror (MM) being controllable to reflect incident electromagnetic radiation along at least two different loci;
        said digital light processor (DLP) focusing means (L2) and stage (STG) for supporting a sample (S) being oriented with respect to one another such that a projected plane of the digital light processor (DLP), a projected plane of the sample (S) surface and a projected plane of the focusing means (L2) intersect, and such that the following condition is substantially met:

$$\mathrm{Tan}(\alpha') = (X-f)/f\,\mathrm{Tan}(\beta');$$

where "X" is the distance from the digital light processor (DLP), at the point at which said beam impinges thereupon, to a center of said focusing means (L2), and "f" is the focal length of said focusing means (L2);
    such that in use said source (LS) of electromagnetic radiation provides an expanding beam (BI) of electromagnetic radiation to said collecting means (L1), which in turn directs electromagnetic radiation onto a sample (S) placed on said stage (STG) for supporting a sample (S); and such that said first focusing means (L2) generates an image of said sample on said digital light processor (DLP);

at least one of said microscopic mirrors (MM) in said digital light processor (DLP) being caused to be oriented to direct electromagnetic radiation incident thereupon to said second focusing means (L3), which in turn focuses electromagnetic radiation provided thereto from said at least one microscopic mirror (MM) onto said at least one detector element (DET) while other of said microscopic mirrors (MM) direct electromagnetic radiation away therefrom;

b) if required for alignment, adjusting the orientations of said stage (STG) for supporting a sample (S), said focusing means (L2) and said detector with respect to one another such that a projected plane of the digital light processor (DLP), a projected plane of the sample (S) surface and a projected plane of the focusing means (L2) intersect along a line, and such that the following condition is substantially met:

$$\operatorname{Tan}(\alpha')=(X-f)/f\operatorname{Tan}(\beta');$$

c) causing said source (LS) of electromagnetic radiation to provide an expanding beam (BI) of electromagnetic radiation to said collecting means (L1), which in turn directs collected electromagnetic radiation onto a sample (S) placed on said stage (STG) for supporting a sample; and causing said first focusing means (L2) to focus collected electromagnetic radiation reflecting from said sample (S);

d) causing at least one of said microscopic mirrors (MM) in said digital light processor (DLP) to be oriented to direct electromagnetic radiation incident thereupon to said second focusing means (L3), which in turn focuses electromagnetic radiation provided thereto from said at least one microscopic mirror (MM) onto said at least one detector element (DET).

6. A method as in claim 5, in which the step of providing at least one detector element (DET), involves providing a single detector element (DET).

7. A method as in claim 5 which further comprises the step of:

d) causing said at least one microscopic mirrors (MM) in said digital light processor (DLP) which was caused to be oriented to direct electromagnetic radiation incident thereupon to said second focusing means (L3) in step c, to be reoriented so as to direct incident electromagnetic radiation away from said at least one detector element (DET); and causing at least one other microscopic mirror (MM) in said digital light processor (DLP) to be oriented to direct electromagnetic radiation incident thereupon to said second focusing means (L3) which in turn focuses electromagnetic radiation provided thereto from said at least one microscopic mirror (MM) onto said at least one detector element (DET), which in turn focuses electromagnetic radiation provided thereto from said at least one microscopic mirror (MM) onto said at least one detector element (DET);

and monitoring the sequential output of said at least one detector element (DET) as the orientations of said microscopic mirrors (MM) are changed and interpreting said output as a sequence of images of different locations on said sample; said method optionally further comprising combining data obtained by practice of steps a-d to provide at least one composite image.

8. A method as in claim 5 in which said method also involves performing at least one selection from the group consisting of:

storing at least some data provided by said at least one detector in machine readable media;

analyzing at least some of the data provided by said at least one detector element and storing at least some of the results of said analysis in machine readable media;

displaying at least some data provided by said at least one detector element by electronic and/or non-electronic means;

analyzing at least some of the data provided by said at least one detector element and displaying at least some of the results of said analysis by electronic and/or non-electronic means;

causing at least some data provided by said at least one detector element to produce a signal which is applied to provide a concrete and tangible result;

analyzing at least some of the data provided by said at least one detector element and causing at least some thereof to produce a signal which is applied to provide a concrete and tangible result.

* * * * *